United States Patent [19]
Narita et al.

[11] Patent Number: 5,795,871
[45] Date of Patent: Aug. 18, 1998

[54] PHARMACEUTICAL COMPOSITION FOR TREATMENT OF NON-SMALL CELL LUNG CANCER

[75] Inventors: Nobuhiro Narita, Uda-gun; Masayoshi Sawaki, Izumi; Keiichi Mikasa, Yao; Eiji Kita, Nara, all of Japan

[73] Assignee: Nobuhiro Narita, Japan

[21] Appl. No.: 727,547

[22] PCT Filed: Apr. 26, 1995

[86] PCT No.: PCT/JP95/00819

§ 371 Date: Oct. 23, 1996

§ 102(e) Date: Oct. 23, 1996

[87] PCT Pub. No.: WO95/28939

PCT Pub. Date: Nov. 2, 1995

[30] Foreign Application Priority Data

Apr. 26, 1994 [JP] Japan .................................. 6-088297

[51] Int. Cl.$^6$ .................................................. A61K 31/70
[52] U.S. Cl. .................................. 514/29; 514/28
[58] Field of Search ................................... 514/28, 29

[56] References Cited

U.S. PATENT DOCUMENTS

| | | | |
|---|---|---|---|
| 4,331,803 | 5/1982 | Watanabe et al. | 514/29 |
| 4,349,545 | 9/1982 | d'Ambrieres et al. | 514/29 |
| 4,517,359 | 5/1985 | Kobrehel et al. | 514/28 |

OTHER PUBLICATIONS

The Merck Index, 7th Ed., 1989,Merck & Co, Inc, Rahway, N.J. pp. 146, 365, 577, 578 and 1316.
Chem. Abst., vol. 96 (1982) Columbus, OH, USA #1869.
Jnci. J. Natl. Cancer Inst. (1981), 67[4], pp. 877–880.

*Primary Examiner*—Jerome D. Goldberg
*Attorney, Agent, or Firm*—Lorusso & Loud

[57] ABSTRACT

14- or 15-membered-ring macrolide compounds such as clarithromycin, erythromycin B, etc. have a potent antitumor effect on non-small cell lung cancers which are considered the most difficult tumors to be be subjected to surgical operation and chemotherapy, and are useful as a practical therapeutic agent of non-small cell lung cancer.

16 Claims, No Drawings

PHARMACEUTICAL COMPOSITION FOR TREATMENT OF NON-SMALL CELL LUNG CANCER

TECHNICAL FIELD

The present invention relates to a pharmaceutical composition effective as an anticancer agent for non-small cell lung cancer comprising a 14- or 15-membered-ring macrolide compound as an effective ingredient.

BACKGROUND ART

In many countries including Japan, Europe and America, the number of patients with lung cancer is fairly large and further increasing year after year with deterioration of atmospheric environment on the earth, contrary to the number of patients with gastric cancer which is reducing year after year. Lung cancers can be histologically classified into non-small cell lung cancers (e.g. squamous cell carcinoma, adeno carcinoma, large cell carcinoma, etc.) and small cell lung cancer. Non-small cell lung cancer has very largely different biological properties and responses to chemotherapeutics from those of small cell lung cancer. Thus, chemotherapeutic formulas are different between these two types of lung cancer.

It is reported that non-small cell lung cancers are the tumors of which chemotherapy is the most difficult, and any useful therapies for advanced inoperable cancers have not been established (Journal of Clinical Oncology, vol. 10, pp. 829–838 (1992)). The combination therapy of cisplatin and interferon is reported (European Journal of Cancer, vol. 30A, No. 1, pp. 11–15 (1994)). However, this remedy can not be widely acceptable because of insufficient therapeutic effect and harmful side effects.

Japanese Patent Kokai 5-163293 refers to some specified antibiotics of 16-membered-ring macrolides as a drug delivery carrier capable of transporting anthoracycline-type anticancer drugs into the lungs for the treatment of lung cancers. However, the macrolide antibiotics specified herein are disclosed to be only a drug carrier, and there is no reference to the therapeutic use of macrolides against non-small cell lung cancers.

WO 93/18652 refers to the effectiveness of the specified 16-membered-ring macrolides such as bafilomycin, etc. in treating non-small cell lung cancers, but they have not yet been clinically practicable.

Pharmacology, vol. 41, pp. 177–183 (1990) describes that a long-term use of erythromycin increases productions of interleukins 1, 2 and 4, all of which contribute to host immune responses, but there is no reference to the effect of this drug on non-small cell lung cancers.

Tetragenesis, Carcinogenesis, and Mutagenesis, vol. 10, pp. 477–501 (1990) describes that some of antimicrobial drugs can be used as an anticancer agent, but does not refer to their application to non-small cell lung cancers.

In addition, interleukins are known to have an antitumor effect, but have not been reported to be effective against non-small cell lung cancers.

Any 14 - or 15-membered-ring macrolides have not been reported to be effective against non-small cell lung cancers.

As stated above, at present, there is no disclosure about practical chemotherapeutic drugs of non-small cell lung cancer, and any chemotherapeutic drugs clinically available are not practicable for the treatment of non-small cell lung cancer. Accordingly, apart from the conventional concept of anticancer chemotherapy, there is a strong need for the development of therapeutic drugs practicably effective for the treatment of non-small cell lung cancers.

DISCLOSURE OF THE INVENTION

As a result of extensive research of antitumor activity of various compounds in order to solve the above problem, unexpectedly, the present inventors have found that certain 14- or 15-membered-ring macrolide compounds have the ability to inhibit the growth and metastasis of non-small cell lung cancers, a useful effect on the malignant tumor which distantly metastasized to other organs and an excellent treatment effect in patients with advanced inoperable non-small cell lung cancers, and improve the quality of life of the patients. Based on these findings, the present invention has been accomplished.

The present invention is a pharmaceutical composition for the treatment of non-small cell lung cancers comprising as an effective ingredient a compound represented by Formula (I):

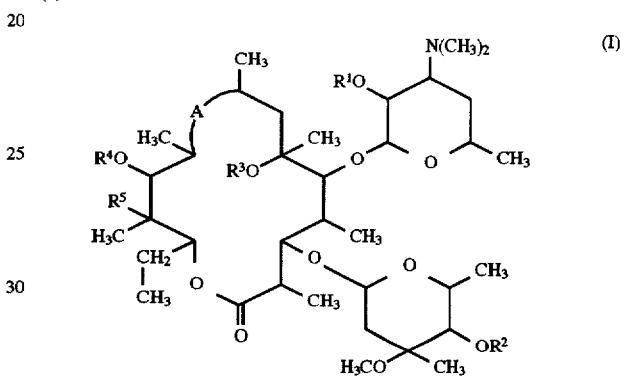

[wherein $R^1$, $R^2$, $R^3$ and $R^4$ are each a hydrogen atom, an optionally substituted alkyl group or an acyl group, $R^5$ is a hydrogen atom or —$OR^6$ (wherein $R^6$ is a hydrogen atom, an optionally substituted alkyl group or an acyl group, or $R^4$ and $R^6$ together form >C=O), and

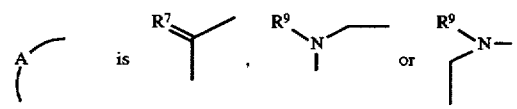

(wherein $R^7$ is an oxygen atom or =N—O—$(CH_2)_{n'}$—X—$R^8$ (wherein n is an integer of 1 to 6, X is an oxygen atom, a sulfur atom or —NY— (wherein Y is a hydrogen atom or an optionally substituted hydrocarbon group), and $R^8$ is an optionally substituted hydrocarbon group) and $R^9$ is a hydrogen atom or an optionally substituted hydrocarbon group)] or a pharmaceutically acceptable salt thereof.

Further, the present invention is a method for the treatment of non-small cell lung cancer comprising administering an effective amount of the compound of Formula (I) or a pharmaceutically acceptable salt thereof to humans.

Furthermore, the present invention is use of the compound of Formula (I) or a pharmaceutically acceptable salt thereof for the manufacture of the pharmaceutical composition for the treatment of non-small cell lung cancer.

In Formula (I), the alkyl group of the optionally substituted alkyl group as defined for $R^1$, $R^2$, $R^3$, $R^4$ and $R^6$ is, for example, a $C_{1-6}$ alkyl group (e.g. methyl, ethyl, propyl, isopropyl, butyl, isobutyl, s-butyl, t-butyl, etc.), preferably a $C_{1-4}$ alkyl group (e.g. methyl, ethyl, propyl, isopropyl, etc.), and particularly preferably a methyl group because of a stronger antitumor activity.

Examples of the substituent of the optionally substituted alkyl group are hydroxyl, amino, carboxyl, nitro, cyano, $C_{1-6}$ alkoxy (e.g. methoxy, ethoxy, propoxy, isopropoxy, etc.), mono-$C_{1-6}$ alkylamino (e.g. methylamino, ethylamino, etc.), di-$C_{1-6}$ alkylamino (e.g. dimethylamino, diethylamino, etc.), $C_{1-6}$ alkyl-carbonyloxy (e.g. acetoxy, ethylcarbonyloxy, etc.), halogen (fluorine, bromine, chlorine, iodine), etc. The alkyl group may optionally have 1 to 3 of these substituents at any available positions, and when there are two or more substituents, they may be the same or different.

The acyl group as defined for $R^1$, $R^2$, $R^3$, $R^4$ and $R^6$ in Formula (I) is, for example, a carboxylic acid acyl group or a sulfonic acid acyl group, and preferably a carboxylic acid acyl group because of a stronger antitumor activity.

The carboxylic acid acyl group is, for example, an acyl group derived from a carboxylic acid, and specifically —CO—$R^a$ (wherein $R^a$ is a hydrogen atom or an optionally substituted hydrocarbon group).

The sulfonic acid acyl group is, for example, an acyl group derived from a sulfonic acid, and specifically —SO$_2$—$R^b$ (wherein $R^b$ is an optionally substituted hydrocarbon group).

The optionally substituted hydrocarbon group for $R^a$ and $R^b$ is the same as the optionally substituted hydrocarbon group defined below.

Preferred examples of the acyl group are a carboxylic acid acyl group such as a formyl group, a $C_{1-6}$ alkyl-carbonyl group (e.g. acetyl, propionyl, etc.), a $C_{2-6}$ alkenyl-carbonyl group (e.g. acryloyl, methacryloyl, etc.) and a $C_{6-14}$ arylcarbonyl group (e.g. benzoyl, etc.); and a sulfonic acid acyl group such as a $C_{1-6}$ alkylsulfonyl group (e.g. methylsulfonyl, ethylsulfonyl, propylsulfonyl, etc.) and the like. The acyl group may optionally have 1 to 3 substituents in any available positions, and examples of the substituent are halogen (fluorine, chlorine, bromine, iodine), hydroxyl, $C_{1-4}$ alkoxy (e.g. methoxy, ethoxy, propoxy, isopropoxy, etc.), amino, cyano, etc. When there are two or more substituents, they may be the same or different.

Examples of the optionally substituted hydrocarbon group as defined for Y, $R^8$ and $R^9$ in Formula (I) are those shown in the following (1) to (5).

(1) a $C_{1-6}$ alkyl group (e.g. methyl, ethyl, propyl, isopropyl, etc.) optionally having 1 to 3 substituents selected from hydroxyl, amino, carboxyl, nitro, cyano, $C_{1-6}$ alkoxy (e.g. methoxy, ethoxy, propoxy, isopropoxy, etc.), mono-$C_{1-6}$ alkylamino (e.g. methylamino, ethylamino, etc.), di-$C_{1-6}$ alkylamino (e.g. dimethylamino, diethylamino, etc.), $C_{1-6}$ alkyl-carbonyloxy (e.g. acetoxy, propionyloxy, etc.) and halogen (fluorine, chlorine, bromine, iodine), (2) a $C_{2-6}$ alkenyl group (e.g. vinyl, allyl, isopropenyl, etc.) optionally having 1 to 3 substituents selected from hydroxyl, amino, carboxyl, nitro, cyano, $C_{1-6}$ alkoxy (e.g. methoxy, ethoxy, propoxy, isopropoxy, etc.), mono-$C_{1-6}$ alkylamino (e.g. methylamino, ethyl-amino, etc.), di-$C_{1-6}$ alkylamino (e.g. dimethylamino, diethylamino, etc.), $C_{1-6}$ alkyl-carbonyloxy (e.g. acetoxy, propionyloxy, etc.) and halogen (fluorine, chlorine, bromine, iodine), (3) a $C_{2-6}$ alkinyl group (e.g. ethinyl, 2-propinyl, 2-butinyl, etc.) optionally having 1 to 3 substituents selected from hydroxyl, amino, carboxyl, nitro, cyano, $C_{1-6}$ alkoxy (e.g. methoxy, ethoxy, propoxy, isopropoxy, etc.), mono-$C_{1-6}$ alkylamino (e.g. methylamino, ethylamino, etc.), di-$C_{1-6}$ alkylamino (e.g. dimethylamino, diethylamino, etc.), $C_{1-6}$ alkyl-carbonyloxy (e.g. acetoxy, propionyloxy, etc.) and halogen (fluorine, chlorine, bromine, iodine), (4) a $C_{6-14}$ aryl group (e.g. phenyl, etc.) optionally having 1 to 5 substituents selected from (a) a $C_{1-6}$ alkyl group (e.g. methyl, ethyl, propyl, iso-propyl, etc.) optionally having 1 to 3 substituents selected from hydroxyl, amino, carboxyl, nitro, cyano, $C_{1-6}$ alkoxy (e.g. methoxy, ethoxy, propoxy, isopropoxy, etc.), mono-$C_{1-6}$ alkylamino (e.g. methylamino, ethyl-amino, etc.), di-$C_{1-6}$ alkylamino (e.g. dimethylamino, diethylamino, etc.), $C_{1-6}$ alkyl-carbonyloxy (e.g. acetoxy, propionyloxy, etc.) and halogen (fluorine, chlorine, bromine, iodine), (b) mono- or di-$C_{1-6}$ alkylamino (e.g. methylamino, ethylamino, dimethylamino, diethylamino, etc.), (c) $C_{1-6}$ alkyl-carbonylamino (e.g. acetylamino, etc.), (d) hydroxyl, (e) carboxyl, (f) nitro, (g) cyano, (h) $C_{1-6}$ alkoxy (e.g. methoxy, ethoxy, propoxy, isopropoxy, etc.), (i) $C_{1-6}$ alkyl-carbonyloxy (e.g. acetoxy, propionyloxy, etc.) and (j) halogen (fluorine, chlorine, bromine, iodine), and (5) a $C_{7-16}$ aralkyl group (e.g. benzyl, etc.) optionally having 1 to 5 substituents selected from (a) a $C_{1-6}$ alkyl group (e.g. methyl, ethyl, propyl, isopropyl, etc.) optionally having 1 to 3 substituents selected from hydroxyl, amino, carboxyl, nitro, cyano, $C_{1-6}$ alkoxy (e.g. methoxy, ethoxy, propoxy, isopropoxy, etc.), mono-$C_{1-6}$ alkylamino (e.g. methylamino, ethyl-amino, etc.), di-$C_{1-6}$ alkylamino (e.g. dimethylamino, diethylamino, etc.), $C_{1-6}$ alkyl-carbonyloxy (e.g. acetoxy, propionyloxy, etc.) and halogen (fluorine, chlorine, bromine, iodine), (b) mono- or di-$C_{1-6}$ alkylamino (e.g. methylamino, ethylamino, dimethylamino, diethylamino, etc.), (c) $C_{1-6}$ alkyl-carbonylamino (e.g. acetylamino, etc.), (d) hydroxyl, (e) carboxyl, (f) nitro, (g) cyano, (h) $C_{1-6}$ alkoxy (e.g. methoxy, ethoxy, propoxy, isopropoxy, etc.), (i) $C_{1-6}$ alkyl-carbonyloxy (e.g. acetoxy, propionyloxy, etc.) and (j) halogen (fluorine, chlorine, bromine, iodine).

The optionally substituted hydrocarbon group is preferably a $C_{1-6}$ alkyl group (e.g. methyl, ethyl, propyl, isopropyl, etc.) optionally having 1 to 3 substituents selected from hydroxyl, amino, carboxyl, nitro, cyano, $C_{1-6}$ alkoxy (e.g. methoxy, ethoxy, propoxy, isopropoxy, etc.), mono-$C_{1-6}$ alkylamino (e.g. methylamino, ethylamino, etc.), di-$C_{1-6}$ alkylamino (e.g. dimethylamino, diethylamino, etc.), $C_{1-6}$ alkyl-carbonyloxy (e.g. acetoxy, propionyloxy, etc.) and halogen (fluorine, chlorine, bromine, iodine).

The $C_{1-6}$ alkyl group, the $C_{2-6}$ alkenyl group, the $C_{2-6}$ alkinyl group, the $C_{6-14}$ aryl group and the $C_{7-16}$ aralkyl group as exemplified above for the optionally substituted hydrocarbon group are those optionally having substituents at any available positions, and when there are two or more substituents, they may be the same or different.

$R^1$, $R^2$, $R^3$ and $R^4$ are preferably each a hydrogen atom or a $C_{1-4}$ alkyl group (e.g. methyl, ethyl, propyl, isopropyl, etc.), and more preferably each a hydrogen atom or a methyl group because of a stronger antitumor activity.

$R^5$ is preferably a hydrogen atom or —$OR^6$ (wherein $R^6$ is a hydrogen atom or a $C_{1-4}$ alkyl group such as methyl, ethyl, propyl, isopropyl, etc.), and more preferably a hydrogen atom, a hydroxyl group or a methoxy group because of a stronger antitumor activity.

Preferably, $R^7$ is an oxygen atom or =N—O—(CH$_2$)$^n$—X—$R^8$ [wherein X is an oxygen atom or —$N^a$— (wherein $Y^a$ is a $C_{1-4}$ alkyl group such as methyl, ethyl, propyl, isopropyl, etc.), and $R^8$ is a $C_{1-4}$ alkyl group (e.g. methyl, ethyl, propyl, isopropyl, etc.), a $C_{1-4}$ alkoxy-$C_{1-4}$ alkyl group (e.g. methoxymethyl, methoxy-ethyl, ethoxymethyl, ethoxyethyl, etc.), and n is an integer of 1 to 4] because of a stronger antitumor activity.

$R^9$ is preferably a hydrogen atom, a $C_{1-4}$ alkyl group (e.g. methyl, ethyl, propyl, isopropyl, etc.), or the $C_{2-4}$ alkenyl group (e.g. vinyl, allyl, isopropenyl, etc.), and more preferably a $C_{1-4}$ alkyl group (e.g. methyl, etc.) because of a stronger antitumor activity.

Examples of the compound of Formula (I) or salt thereof having a good therapeutic effect on non-small cell lung cancer are the following two Compounds A) and B).

Compound A): A compound of Formula (I) wherein $R^1$, $R^2$, $R^3$ and $R^4$ are each a hydrogen atom or a $C_{1-4}$ alkyl group, $R^5$ is a hydrogen atom or —$OR^{6a}$ (wherein $R^{6a}$ is a hydrogen atom or a $C_{1-4}$ alkyl group), and

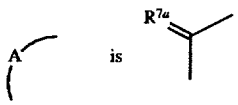

[wherein $R^{7a}$ is an oxygen atom or =N—O—$(CH_2)^m$—O—$R^{8a}$ (wherein m is an integer of 1 to 4, and $R^{8a}$ is a $C_{1-4}$ alkoxy-$C_{1-4}$ alkyl group)] or a salt thereof.

Compound B) : A compound of Formula (I) wherein $R^1$, $R^2$, $R^3$ and $R^4$ are each a hydrogen atom or a $C_{1-4}$ alkyl group, $R^5$ is a hydrogen atom or —$OR^{6a}$ (wherein $R^{6a}$ is a hydrogen atom or a $C_{1-4}$ alkyl group), and

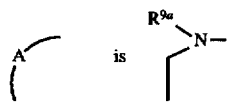

(wherein $R^{9a}$ is a hydrogen atom, a $C_{1-4}$ alkyl or a $C_{2-4}$ alkenyl group) or a salt thereof.

In Compounds A) and B), the $C_{1-4}$ alkyl group as defined for $R^1$, $R^2$, $R^3$, $R^4$ and $R^6$ is preferably a methyl, the $C_{1-4}$ alkoxy-$C_{1-4}$ alkyl group as defined for $R^{8a}$ is preferably a methoxymethyl group, and the $C_{2-4}$ alkenyl group as defined for $R^{9a}$ is preferably a vinyl group.

The compounds of Formula (I) or salts thereof contain isomers thereof, but preferably natural-type because of a stronger antitumor activity.

Preferable compounds of the present invention are, for example, erythromycin A ($R^1$, $R^2$, $R^3$ and $R^4$ are each a hydrogen atom, $R^5$ is a hydroxyl group and -A- is >C=O in Formula (I)), erythromycin B ($R^1$, $R^2$, $R^3$, $R^4$ and $R^5$ are each a hydrogen atom, and —A— is >C=O in Formula (I)), clarithromycin ($R^1$, $R^2$ and $R^4$ are each a hydrogen atom, $R^3$ is a methyl group, $R^5$ is a hydroxyl group, and —A— is >C=O in Formula (I)), roxithromycin ($R^1$, $R^2$, $R^3$ are $R^4$ are each a hydrogen atom, $R^5$ is a hydroxyl group, and —A— is >=N=OCH$_2$OCH$_2$CH$_2$OCH$_3$ in Formula (I)) and azithromycin ($R^1$, $R^2$, $R^3$ and $R^4$ are each a hydrogen atom, $R^5$ is a hydroxyl group, and —A— is

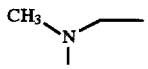

in Formula (I)), and erythromycin A and clarithromycin are more preferable because of establishing clinically therapeutic effect on non-small cell lung cancer in the present invention.

Examples of the pharmaceutically acceptable salt of the compound of the present invention are salts with inorganic acids (e.g. hydrochloride, sulfate, phosphate, diphosphate, hydrobromide, nitrate, etc.) and salts with organic acids (e.g. acetate, malate, maleate, fumarate, tartrate, succinate, citrate, butyrate, methanesulfonate, p-toluenesulfonate, palmitate, salicylate, lactobionate, stearate, etc.) without, however, being limited thereby.

The compounds of the present invention or pharmaceutically acceptable salts thereof can be prepared, for example, by the methods described in U.S. Pat. Nos. 2,823,203, 4,331,803, 4,349,545 and 4,517,359, Tetrahedron Lett., vol. 34, No. 31, pp. 4913–4916 (1993), Journal of Synthetic Organic Chemistry, vol. 38, No. 4, pp. 395–414 (1980) or modifications thereof.

The compounds of the present invention and pharmaceutically acceptable salts thereof have the therapeutic effect on intractable solid cancers such as non-small cell lung cancer in humans and other mammals (e.g. rats, mice, rabbits, dogs, cats, cows, pigs, etc.), and can be used as their bulks because of low toxicity, but usually as dosage forms for the treatment of non-small cell cancer prepared by using pharmaceutically acceptable carriers in the same manner as other antibiotics are prepared. The pharmaceutically acceptable carriers to be used are appropriately chosen from excipients (e.g. calcium carbonate, kaolin, sodium bicarbonate, lactose, starches, crystalline cellulose, talc, granulated sugar, porous materials, etc.), binders (e.g. dextrin, gums, α-starch, gelatin, hydroxypropylcellulose, hydroxypropylmethylcellulose, pullulan, etc.), disintegrators (e.g. carboxymethylcellulose calcium, croscarmellose sodium, crospovidone, low substituted hydroxypropylcellulose, starch partially in the α-form, etc.), lubricants (e.g. magnesium stearate, calcium stearate, talc, starch, sodium benzoate, etc.), coloring agents (e.g. tar color, caramel, iron sesquioxide, titanium oxide, riboflavins, etc.), corrigents (e.g. sweetening agents, flavoring agents, etc.), stabilizers (e.g. sodium sulfite, etc.) and preservatives (e.g. parabens, sorbic acid, etc.).

The pharmaceutical composition of the present invention contains the compound of Formula (I) or a salt thereof in the same amount as it is used as an anti-bacterial agent. Usually, the amount of the compound of Formula (I) or a salt thereof is 0.1 to 100% by weight based on the total weight of the composition, specifically 20 to 100% by weight in case of the solid form such as capsules, tablets, granules, etc., and 5 to 30% by weight in case of the liquid form such as injections, etc. because of stability of the preparations. Examples of the dosage form are tablets (including sugar-coated tablets, film-coated tablets, etc.), pills, capsules, granules, fine granules, powders, syrups, emulsions, suspensions, injections, etc. These preparations can be prepared by conventional methods such as the methods described in Japanese Pharmacopoeia, etc. Specifically, tablets can be prepared by granulating a homogeneous mixture of the compound of the present invention with an excipient, a binder, a disintegrator or other appropriate additives, adding a lubricant and the like, and compressing the mixture for shaping. Alternatively, tablets can directly be prepared by compressing the compound of the present invention as it is or a homogeneous mixture of it with an excipient, a binder, a disintegrator, suitable additives and the like. If desired, the tablets can contain a coloring agent, a corrigent and the like. The tablets can be also coated with an appropriate coating agent. Injection can be prepared by charging a container with a suitable amount of a solution, a suspension or an emulsion of a suitable amount of the compound of the present invention in an aqueous solvent (e.g. water for injection, physiological saline, Ringer's solution, etc.) or in non-aqueous solvent(e.g. vegetable oils, etc.), or a suitable amount of the compound of the present invention, and then sealing the container.

Examples of the carrier for oral compositions are conventional materials in pharmaceutical preparations such as starch, mannitol, crystalline cellulose and sodium carboxymethylcellulose, etc. Examples of the carrier for injections are distilled water, physiological saline, glucose solution and transfusion solutions such as sugar solution, electrolyte solution, amino acid solution, albumin, etc. Furthermore, other additives usually used in pharmaceutical preparations can appropriately be also added.

The above-mentioned preparations can appropriately contain suitable amounts of other anticancers (e.g. ifosfmide, mitomycin C, vindesine, cisplatin, vinblastine, procarbazine, vincristine, adriamycin, etc.) or antibiotics (e.g. penicillin G, takesulin, pansporin, amphotericin B, miconazol, sulfamethaxasole, trimethoprim, josamycin, etc.).

The dose of the pharmaceutical composition of the present invention depends on the patient's age, body weight, severity of the disease, administration route, administration frequency and the like, but for example, it is 0.1 to 100 mg/kg, preferably 0.5 to 10 mg/kg per day of the compound (I) or a salt thereof for an adult patient with non-small cell lung cancer, and more preferably each 200 mg twice per day for an adult person weighing 60 kg. The administration route may be oral or parenteral.

BEST MODE FOR CARRYING OUT THE INVENTION

The present invention is illustrated in more detail by the following experiments and examples without, however, being limited thereby.

Experiment 1 Antitumor Effect on Mouse Ehrlich Ascites Carcinoma EAC

Mouse Ehrlich ascites carcinoma EAC cells ($5\times10^6$) were subcutaneously transplanted to ddy mice (7 weeks old). After 7 days, a control group received 0.9% ethanol orally every day during the survival time. An administration group received erythromycin A dissolved in the same vehicle similarly. For comparison, an untreated group was also inquired. Each group consists of 10 mice. 30 Days after the transplantation, the survival rate (%) of mice as well as the mean survival time (MST) were determined, and the results are together shown in Table 1.

Experiment 2 Antitumor Effect on Mouse Leukemia P388

Mouse leukemia P388 cells ($10^6$) were abdominally transplanted to CDF1 mice (7 weeks old). The administration of erythromycin A was started on the next day. The test was carried out in the same manner as that of Experiment 1, and the results are shown in Table 1.

TABLE 1

Antitumor effect on mouse Ehrlich ascites carcinoma EAC and mouse leukemia P388

| Dose of ery-thromycin (mg/kg) | EAC (ddy mice) | | P388 (CDF1 mice) | |
|---|---|---|---|---|
| | Survival rate (%) 30 days | MST (day) | Survival rate (%) 30 days | MST (day) |
| 1 | 43* | 38.2 | 57* | 36.2 |
| 5 | 63** | 42.7 | 77** | 43.6 |
| 10 | 30* | 30.8 | 33* | 36.8 |
| Vehicle-control | 0 | 23.6 | 0 | 11.9 |
| Untreated | 0 | 24.2 | 0 | 12.3 |

*<0.5, **<0.05

As shown in Table 1, in case of the vehicle-control group, the survival rate after 30 days is 0%, and the mean survival time is short (23.6 days). On the contrary, in case of the erythromycin A (5 mg/kg) administration group, the survival rate after 30 days is 63%, and the mean survival time is long (42.7 days). Furthermore, in case of the untreated group, the survival rate after 30 days is 0%, and the mean survival time is also short (24.2 days).

It is found from these results that erythromycin A has a prolonged survival effect against EAC- and P388-transplanting mice, and an inhibitory effect on the growth of the cancer cells.

Experiment 3 Clinical Effect in Patients With Primary Multiple Non-Small Cell Lung Cancer A man, 70 years old, 163 cm in high, weighing 55 kg, with primary multiple non-small cell lung cancer was administered orally with erythromycin A every day, and there was no recurrence for 5 years after the therapy.

Experiment 4 Clinical Effect in Patients With Primary Multiple Non-Small Cell Lung Cancer Fifty patients, 41 to 82 years old, with III to IV stages of primary non-small cell lung cancers regarded as inoperable (43 patients with non-small cell lung cancer and 7 patients with small cell lung cancer) were randomly divided into an clarithromycin (CAM) administration group, which was orally administered with 200 mg of CAM twice every day, and a non-administration group. The survival time after the therapy of the patients of both groups was observed, and a survival curve was drawn according to the method of Kaplan-Maier, and thereby giving the 50% survival time. Results are shown in Table 2.

TABLE 2

| Group | case | 50% survival time |
|---|---|---|
| Comparison of therapeutic effect in patients with non-small cell lung cancer | | |
| CAM administration group | 22 | 930 days |
| CAM non-administration group | 21 | 299 days |
| Comparison of therapeutic effect in patients with small cell lung cancer | | |
| CAM administration group | 3 | 246 days |
| CAM non-administration group | 4 | 251 days |

As shown in Table 2, in case of the patients with non-small cell lung cancer, the 50% survival time is 930 days in the CAM administration group, contrary to 299 days in the CAM non-administration group. It is established from the results that the survival time of the CAM administration patients is prolonged much longer than that of the CAM non-administration patients. On the other hand, there is confirmed no difference between both groups in case of the patients with small cell lung cancer. It is found from the fact that CAM has an excellent therapeutic effect in patients with non-small lung cell cancer only.

It is also observed that the CAM administration patients are good in terms of appetite, general conditions and the activity of daily living (ADL), show sluggish progress of disease, and improve the quality of life (QOL) by administration of CAM. In addition, the safety of a long-term administration of CAM to humans is already demonstrated (Chemotherapy, vol. 42, pp. 430–435 (1994)), and the side effects were not found in the above clinical experiments.

Example 1 Preparation of Coated Tablets

Composition (Per Coated Tablet)

| | | |
|---|---|---|
| (1) Erythromycin A | 20.0 mg | |
| (2) Lactose | 80.0 mg | |
| (3) Corn Starch | 45.0 mg | |
| (4) Gelatin | 3.0 mg | |
| (5) Magnesium stearate | 2.0 mg | |

A mixture of 20.0 mg of erythromycin A, 80.0 mg of lactose and 45.0 mg of corn starch was granulated using 0.03 ml of 10% aqueous gelatin solution (containing 3.0 mg of gelatin), sifted through a 1 mm-mesh sieve, dried at 40° C., and sifted again. The thus-obtained granules were mixed with 2.0 mg of magnesium stearate and compressed. The resulting core tablet was sugar-coated with an aqueous solution of sucrose, titanium oxide, talc and gum arabic, and polished with yellow bees wax to give a coated tablet.

Example 2 Preparation of Tablet

| Composition (per tablet) | |
|---|---|
| (1) Clarithromycin | 20.0 mg |
| (2) Lactose | 70.0 mg |
| (3) Corn Starch | 50.0 mg |
| (4) Soluble starch | 7.0 mg |
| (5) Magnesium stearate | 3.0 mg |

20.0 mg of clarithromycin and an 3.0 mg of magnesium stearate were granulated using 0.07 ml of 10% aqueous solution of soluble starch (containing 7.0 mg of gelatin), dried and mixed with 70.0 mg of lactose and 50.0 mg of corn starch. The mixture was compressed to give a tablet.

Example 3 Preparation of Injection Solution

| Composition (per ampule) | |
|---|---|
| (1) Erythromycin A | 5.0 mg |
| (2) Lactobionic acid | 2.5 mg |
| (3) Sodium chloride | 20.0 mg |
| (4) Distilled water | ad 2 ml. |

5.0 mg of erythromycin A, 2.5 mg of lactobionic acid, 20.0 mg of sodium chloride were mixed to distilled water to a total volume of 2.0 ml. The solution was filtered and charged into a 2 ml-ampule under aseptic conditions. The ampule was sterilized and sealed to obtain an injection solution.

INDUSTRIAL UTILIZABILITY

The pharmaceutical composition comprising the compound of Formula (I) or a pharmaceutically acceptable salt thereof of the present invention has a great effect against non-small cell lung cancers which have been considered the most difficult tumors to be subjected to surgical operation and chemotherapy, and is useful as a practical therapeutic agent of non-small cell lung cancers. In addition, it can be used safely without side effects which induce serious conditions unlike the previously used anticancer agents.

We claim:

1. A method for the treatment of non-small cell lung cancer in a human comprising:

administering to said human an effective amount of a compound represented by the formula:

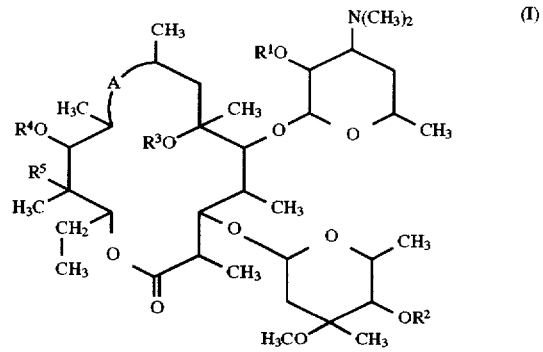

wherein $R^1$, $R^2$, $R^3$ and $R^4$ are each a hydrogen atom, an optionally substituted alkyl group or an acyl group, $R^5$ is a hydrogen atom or —$OR^6$ (wherein $R^6$ is a hydrogen atom, an optionally substituted alkyl group or an acyl group, or $R^4$ and $R^6$ together form >C=O), and

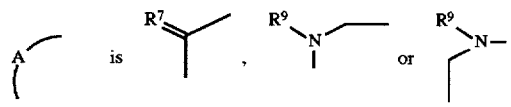

wherein $R^7$ is an oxygen atom or =N—O—$(CH_2)_n$—X—$R^8$, wherein:

n is an integer of 1 to 6,

X is an oxygen atom, a sulfur atom or —NY—, (wherein Y is a hydrogen atom or an optionally substituted hydrocarbon group), and $R^8$ is an optionally substituted hydrocarbon group; and wherein $R^9$ is a hydrogen atom or an optionally substituted hydrocarbon group; or a pharmaceutically acceptable salt thereof.

2. The method according to claim 1, wherein the optionally substituted alkyl group for $R^1$, $R^2$, $R^3$, $R^4$ and $R^6$ is a $C_{1-6}$ alkyl group optionally having 1 to 3 substituents selected from hydroxyl, amino, carboxyl, nitro, cyano, $C_{1-6}$ alkoxy, mono-$C_{1-6}$ alkylamino, di-$C_{1-6}$ alkylamino, $C_{1-6}$ alkyl-carbonyloxy and halogen.

3. The method according to claim 1, wherein the acyl group for $R^1$, $R^2$, $R^3$, $R^4$ and $R^6$ is a formyl group; or a $C_{1-6}$ alkyl-carbonyl group, a $C_{2-6}$ alkenyl-carbonyl group, a $C_{6-14}$ aryl-carbonyl group or a $C_{1-6}$ alkyl-sulfonyl group, each of which may optionally have 1 to 3 substituents selected from halogen, hydroxyl, $C_{1-6}$ alkoxy, amino and cyano.

4. The method according to claim 1, wherein the optionally substituted hydrocarbon group for Y, $R^8$ and $R^9$ is (1) a $C_{1-6}$ alkyl group optionally having 1 to 3 substituents selected from hydroxyl, amino, carboxyl, nitro, cyano, $C_{1-6}$ alkoxy, mono-$C_{1-6}$ alkylamino, di-$C_{1-6}$ alkylamino, $C_{1-6}$ alkyl-carbonyloxy and halogen, (2) a $C_{2-6}$ alkenyl group optionally having 1 to 3 substituents selected from hydroxyl, amino, carboxyl, nitro, cyano, $C_{1-6}$ alkoxy, mono-$C_{1-6}$ alkylamino, di-$C_{1-6}$ alkylamino, $C_{1-6}$ alkyl-carbonyloxy and halogen, (3) a $C_{2-6}$ alkinyl group optionally having 1 to 3 substituents selected from hydroxyl, amino, carboxyl, nitro, cyano, $C_{1-6}$ alkoxy, mono-$C_{1-6}$ alkylamino, di-$C_{1-6}$ alkylamino, $C_{1-6}$ alkyl-carbonyloxy and halogen, (4) a $C^{6-14}$ aryl group optionally having 1 to 5 substituents selected from (a) a $C_{1-6}$ alkyl group optionally having 1 to 3 substituents selected from hydroxyl, amino, carboxyl, nitro, mono-$C_{1-6}$ alkylamino, di-$C_{1-6}$ alkylamino, $C_{1-6}$ alkyl-carbonyloxy and halogen, (b) mono- or di-$C_{1-6}$ alkylamino, (c) $C_{1-6}$ alkyl-carbonylamino, (d) hydroxyl, (e) carboxyl, (f) nitro, (g) $C_{1-6}$ alkoxy, (h) $C_{1-6}$ alkyl-carbonyloxy and (i) halogen, or (5) A $C_{7-16}$ aralkyl group optionally having 1 to 5 substituents selected from (a) a $C_{1-6}$ alkyl group optionally having 1 to 3 substituents selected from hydroxyl, amino, carboxyl, nitro, mono-$C_{1-6}$ alkylamino, di-$C_{1-6}$ alkylamino, $C_{1-6}$ alkyl-carbonyloxy and halogen, (b) mono- or di-$C_{1-6}$ alkylamino, (c) $C_{1-6}$ alkyl-carbonylamino, (d) hydroxyl, (e) carboxyl, (f) nitro, (g) $C_{1-6}$ alkoxy, (h) $C_{1-6}$ alkyl-carbonyloxy and (i) halogen.

5. The method according to claim 1, wherein the optionally substituted hydrocarbon group for Y, $R^8$ and $R^9$ is a $C_{1-6}$ alkyl group optionally having 1 to 3 substituents selected from hydroxyl, amino, carboxyl, nitro, cyano, $C_{1-6}$ alkoxy, mono-$C_{1-6}$ alkylamino, di-$C_{1-6}$ alkylamino, $C_{1-6}$ alkyl-carbonyloxy and halogen.

6. The method according to claim 1, wherein $R^1$, $R^2$, $R^3$ and $R^4$ are each a hydrogen atom or a $C_{1-4}$ alkyl group.

7. The method according to claim 1, wherein $R^5$ is a hydrogen atom, a hydroxyl group or a methoxy group.

8. The method according to claim 1, wherein $R^7$ is an oxygen atom or $=N-O-(CH_2)_n-X-R^8$ (wherein X is an oxygen atom or $-Ny^a-$ (wherein $y^a$ is a $C_{1-4}$ alkyl group), and $R^8$ is a $C_{1-4}$ alkyl group or a $C_{1-4}$ alkoxy-$C_{1-4}$ alkyl group, and n is an integer of 1 to 4.

9. The method according to claim 1, wherein $R^9$ is a hydrogen atom, a $C_{1-4}$ alkyl group or a $C_{2-4}$ alkenyl group.

10. The method according to claim 1, wherein $R^1$, $R^2$, $R^3$ and $R^4$ are each a hydrogen atom or a $C_{1-4}$ alkyl group, $R^5$ is a hydrogen atom or $-OR^{6a}$ (wherein $R^{6a}$ is a hydrogen atom or a $C_{1-4}$ alkyl group), and

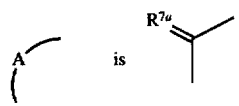

[wherein $R^{7a}$ is an oxygen atom or $=N-O-(CH_2)_m-O-R^{8a}$ (wherein m is an integer of 1 to 4, $R^{8a}$ is a $C_{1-4}$ alkoxy-$C_{1-4}$ alkyl group)].

11. The method according to claim 1, wherein $R^1$, $R^2$, $R^3$ and $R^4$ are each a hydrogen atom or a $C_{1-4}$ alkyl group, $R^5$ is a hydrogen atom or $-OR^{6a}$ (wherein $R^{6a}$ is a hydrogen atom or a $C_{1-4}$ alkyl group), and

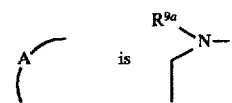

[wherein $R^{9a}$ is a hydrogen atom, a $C_{1-4}$ alkyl group or a $C_{1-4}$ alkenyl group).

12. The method of claim 1 wherein said compound is erythromycin A.

13. The method of claim 1 wherein said compound is erythromycin B.

14. The method of claim 1 wherein said compound is clarithromycin.

15. The method of claim 1 wherein said compound is roxithromycin.

16. The method of claim 1 wherein said compound is azithromycin.

* * * * *

UNITED STATES PATENT AND TRADEMARK OFFICE
CERTIFICATE OF CORRECTION

PATENT NO. : 5,795,871
DATED : August 18, 1998
INVENTOR(S) : NARITA et al

It is certified that error appears in the above-indentified patent and that said Letters Patent is hereby corrected as shown below:

Col. 4, line 55, "$(CH_2)^n$" should read --$(CH_2)_n$--;

line 56, "$N^a$" should read --$NY^a$--; and line 60, "methoxy-ethyl" should read --methoxyethyl--.

Col. 5, line 14, "$(CH_2)^m$" should read --$(CH_2)_m$--.

Signed and Sealed this

Twenty-second Day of June, 1999

*Attest:*

Q. TODD DICKINSON

*Attesting Officer*    Acting Commissioner of Patents and Trademarks